United States Patent
Zhang et al.

(10) Patent No.: US 11,436,824 B2
(45) Date of Patent: Sep. 6, 2022

(54) WATER STRESS DETECTION METHOD FOR TOMATOES IN SEEDLING STAGE BASED ON MICRO-CT AND POLARIZATION-HYPERSPECTRAL IMAGING MULTI-FEATURE FUSION

(71) Applicant: JIANGSU UNIVERSITY, Jiangsu (CN)

(72) Inventors: Xiaodong Zhang, Jiangsu (CN); Hanping Mao, Jiangsu (CN); Hongyan Gao, Jiangsu (CN); Zhiyu Zuo, Jiangsu (CN); Yixue Zhang, Jiangsu (CN)

(73) Assignee: JIANGSU UNIVERSITY, Jiangsu (CN)

( * ) Notice: Subject to any disclaimer, the term of this patent is extended or adjusted under 35 U.S.C. 154(b) by 181 days.

(21) Appl. No.: 16/646,351

(22) PCT Filed: Dec. 19, 2017

(86) PCT No.: PCT/CN2017/117189
§ 371 (c)(1),
(2) Date: Mar. 11, 2020

(87) PCT Pub. No.: WO2019/109383
PCT Pub. Date: Jun. 13, 2019

(65) Prior Publication Data
US 2020/0272817 A1    Aug. 27, 2020

(30) Foreign Application Priority Data
Dec. 5, 2017   (CN) .......................... 201711269627.7

(51) Int. Cl.
*G06K 9/00*        (2022.01)
*G06V 20/10*       (2022.01)
(Continued)

(52) U.S. Cl.
CPC ........... *G06V 20/188* (2022.01); *A01G 7/045* (2013.01); *A01G 31/00* (2013.01); *G01N 21/21* (2013.01);
(Continued)

(58) Field of Classification Search
CPC .. G06K 9/00657; G06K 9/2027; G06K 9/209; A01G 7/045; A01G 31/00;
(Continued)

(56) References Cited

FOREIGN PATENT DOCUMENTS

| CN | 102384767 A | 3/2012 | |
| CN | 103018179   | * 4/2013 | ......... G06K 9/00657 |

(Continued)

*Primary Examiner* — Avinash Yentrapati
(74) *Attorney, Agent, or Firm* — Saliwanchik, Lloyd & Eisenschenk

(57) ABSTRACT

A water stress detection method for tomatoes in a seedling stage based on micro-CT and polarization-hyperspectral imaging multi-feature fusion, comprising: using micro-CT to scan microscopic morphological features such as water stress stomata, spongy body, palisade tissue, cilia, vascular bundle, root volume, main root, and root hair density of tomatoes; using a polarization-hyperspectral imaging system to obtain macroscopic morphological features such as crown width, plant height, and leaf inclination of water stress plants, as well as leaf vein distribution, average gray, and leaf margin shaded area under a water-sensitive wavelength of 1450 nm, and macroscopic morphological features such as polarization states, stock vectors, and Mueller matrix variables of 1450 nm feature images at 0°, 45°, 90°, 135°, and 180° feature polarization angles. By fusion of internal and external structures, above-ground, underground, and macroscopic and microscopic morphological features of water stress tomatoes, and mutual fusion of water stress feature wavelength images and polarization state features, advantages are complementary, comprehensive and precise (Continued)

extraction and precise quantitative analysis of water stress features of the tomatoes are implemented, and a basis for scientific management of water and fertilizer integration of facilities is provided.

5 Claims, 2 Drawing Sheets

(51) Int. Cl.
*A01G 7/04* (2006.01)
*A01G 31/00* (2018.01)
*G01N 21/21* (2006.01)
*G01N 23/046* (2018.01)
*G01N 23/2251* (2018.01)
*G01N 33/00* (2006.01)
*G06T 7/00* (2017.01)
*G06V 10/141* (2022.01)
*G06V 10/147* (2022.01)

(52) U.S. Cl.
CPC ....... *G01N 23/046* (2013.01); *G01N 23/2251* (2013.01); *G01N 33/0098* (2013.01); *G06T 7/0004* (2013.01); *G06V 10/141* (2022.01); *G06V 10/147* (2022.01); *G01N 2223/1016* (2013.01); *G01N 2223/612* (2013.01); *G06T 2207/30128* (2013.01)

(58) Field of Classification Search
CPC .. G01N 21/21; G01N 23/046; G01N 23/2251; G01N 33/0098; G01N 2223/1016; G01N 2223/612; G06T 7/0004; G06T 2207/30128
See application file for complete search history.

(56) References Cited

FOREIGN PATENT DOCUMENTS

| | | | | | |
|---|---|---|---|---|---|
| CN | 103018179 | A | | 4/2013 | |
| CN | 104457843 | A | | 3/2015 | |
| CN | 104697943 | A | | 6/2015 | |
| CN | 105628466 | A | | 6/2016 | |
| CN | 105869187 | A | | 8/2016 | |
| CN | 106706682 | A | * | 5/2017 | ............ A01G 31/00 |
| CN | 106706682 | A | | 5/2017 | |
| CN | 106885812 | A | * | 6/2017 | ........... G01N 23/046 |
| CN | 106885812 | A | | 6/2017 | |
| WO | 2007129648 | A1 | | 11/2007 | |
| WO | 2010072876 | A1 | | 7/2010 | |

* cited by examiner

WATER STRESS DETECTION METHOD FOR TOMATOES IN SEEDLING STAGE BASED ON MICRO-CT AND POLARIZATION-HYPERSPECTRAL IMAGING MULTI-FEATURE FUSION

CROSS REFERENCE TO RELATED APPLICATIONS

This application is a National Stage Application of International Application Number PCT/CN2017/117189, filed Dec. 19, 2017; which claims priority to Chinese Application No. 201711269627.7, filed Dec. 5, 2017.

TECHNICAL FIELD

The present invention belongs to the technical field of biological comprehensive information detection in protected agriculture, and relates to a water stress detection technique for tomatoes in seedling stage based on micro-CT and polarization-hyperspectral imaging multi-feature fusion.

BACKGROUND ART

Presently, large-scale, industrialization and intellectualization have become the development directions of facility cultivation and aquaculture, and intelligent monitoring techniques for growing process of greenhouse crops have become a key link in greenhouse production. The water stress state of plants is an important basis for intelligent water and fertilizer management in greenhouses. Plant nutrition and water detection methods, such as traditional empirical detection method and chemical analysis, canopy-air temperature difference and image detection methods, etc., have problems such as high labor intensity, long detection cycle, high susceptibility to environmental interferences, and low detection accuracy, etc., may lead to misjudgments easily, are unable to meet meet the requirements of modern facility production. In recent years, micro-CT technology has emerged and has been applied preliminarily in agricultural engineering as the science and technology are further developed and the costs of high-tech equipment are further reduced. Micro-CT technology can realize accurate phenotype of the internal and external micro-morphological differences among plants incurred by water stress through high-precision perspective scanning and three-dimensional imaging, while polarization-hyperspectral imaging technology can detect water stress differences such as apparent color/texture/polarization state and so on, micro-structures of tomatoes such as cilia and surface crimples, etc. Thus, through fusion and complementation of internal and external features, accurate detection for water stress of tomatoes can be realized, and has important theoretical significance and application value for improving the technical level of intellectualization of greenhouse production.

Though CT technology has been widely applied in the field of medical detection, micro-CT is seldom applied yet in production process monitoring techniques for protected agriculture. Presently, some researchers have utilized micro-CT in researches on soil and root system detection. Among the researches, the invention patent application No. 201710189744.6 has disclosed a method and an apparatus based on CT technology for detecting the damage of seedling pot in the crop seedling holding and picking process, which utilize a CT scanner to perform tomoscan of potted crop seedlings in different holding and picking states, and extract and three-dimensionally visualize the pores in the seedling pot, to study the generation and expansion of new pores and cracks in the seedling pot and thereby provide a basis for the structural design of end-effector for picking seedling and the selection of holding and picking parameters. The invention patent application No. 201611253837.2 has disclosed a seedling raising method for CT scanning of potted crop seedling and three-dimensional reconstruction and imaging of root system. The method enables the root system of potted crop seedling to absorb a CT contrast agent, without destroying the spatial distribution of the root system in the nursery substrate, so that the density of root system is higher than that of the nursery substrate. The attenuation in the root system is different from that in the nursery substrate in the CT scanning process. As a result, there is an obvious difference between the greyscale of the root system and the greyscale of the nursery substrate in the generated tomographic image. The root system is separated from the nursery substrate by performing threshold segmentation of the tomography image, and thereby a three-dimensional image of the root system with higher integrity and definition is generated. In the aspect of soil detection, the researches made by Rachman et al. demonstrate that the macroporosity measured with the CT scanning method is very close to the result obtained with a traditional soil water retention reckoning method; Udawatta et al. have studied the influences of different grassland restoration methods and farmlands on the characteristics of pores in soil with a CT scanning and image analysis method, the results indicate that grassland restoration has promoted the improvement of soil pore parameters such as pore quantity, porosity, round rate and fractal dimensions, etc.

Polarization imaging technology refers to utilizing the polarized light reflected and scattered from all points on the surface of the detected object for imaging. Different objects or different states of the same object such as roughness, voidage, water content, physical and chemical properties of the constituent material and so on, will generate characteristic polarization determined by their own properties and basic laws of optics, and generate different polarization states, which have a close relationship with the wavelength; thus, polarization images are formed. Polarization images have advantages that ordinary images and reflective spectra do not possess, and can characterize some information that is very difficult for intensity images and spectra to characterize, such as changes in the micro-structures of the target surface, selective absorption and scattering of incident light in the material, as well as changes in the characteristics of forward reflection, backward reflection and diffuse reflection on the surface of the object. Therefore, polarization imaging technology has broad military and civil application prospects. Polarization imaging technology has become a hotspot in researches around the world, owing to its unique characteristics.

In recent years, polarization detection technology has developed rapidly, and it has been developed from simple linear polarization detection to full Stokes parameter measurement nowadays. To answer the question that whether polarization detection has advantages that traditional photometric detection does not have, Raven et al. measured the polarization characteristics of laurel and mullein respectively. They carried out tests with lasers at 632 nm and 1,064 nm wavelengths, and plotted polarized hemispheric directional reflection curves of laurel and mullein. The results indicated that there were significant differences between the polarization properties of different kinds of leaves. Plant species may be identified by means of polarization remote sensing, utilizing a characteristic that the leaves of different plants have different polarization states for reflected light. The researches made by Vanderbilt et al. on corn, sorghum, soybean, wheat, and maple leaves also indicated that the degree of polarization of reflected light included information on the surface and inner layers of the leaves, and the non-polarized components could be used to predict the water content in the leaves excellently. Zhigang Han et al. studied the polarized reflection characteristics of sunlight of Chinese wildrye and Carex, and believed that polarization measurement could obtain some specular reflection characteristics, which could not be obtained by means of some traditional intensity measurement. Hu Zhao et al. studied the multi-angle polarization characteristics of soil. The results indicated that the polarization characteristics of soil were strongly influenced by the moisture content in the soil.

In summary, micro-CT technology can be used for accurate analysis of micro-morphological differences of detected objects, owing to its advantages such as high imaging speed, contactless and non-destructive measurement, three-dimensional reconstruction, and accurate visual detection of internal and external microstructures, etc. However, the water stress of tomatoes is not only reflected in the micro-morphological changes of the internal tissues of leaves, stems and root systems, but also reflected in the characteristics of hyperspectral reflection and polarization states resulted from the water stress. The present invention innovatively proposes that accurate and quantitative analysis on water stress of plants can be realized by fusing micro-CT technology and polarization-hyperspectral image technology to obtain morphological features of macro and micro tissues and structures, characteristic hyperspectral images and polarization distribution characteristics under water stress, and quantitative diagnosis of water stress of tomatoes can be realized by fusing morphological features of internal and external structures, above-ground and underground structures, and macro and micro morphological features of the plants and the characteristic wavelength images and polarization states under water stress to utilize their complementary advantages. The method provided in the present invention is an original method, and has not been reported in China or foreign countries.

CONTENTS OF THE INVENTION

The object of the present invention is to provide a water stress detection method for tomatoes in seedling stage based on micro-CT and polarization-hyperspectral multi-feature fusion, in order to realize rapid, non-destructive and accurate detection of water stress state of tomatoes in seedling stage, and provide a basis for scientific management of water and fertilizer in facilities.

To solve the above-mentioned technical problem, the present invention employs the following technical solution:

A water stress detection method for tomatoes in seedling stage based on micro-CT and polarization-hyperspectral imaging multi-feature fusion, including the following steps:

Step 1: using a standard nutrient solution formulation, utilizing pearlite as a substrate, employing soilless cultivation to plant tomatoes, and managing the tomatoes with standardized management methods of greenhouse to ensure normal supply of nutrient elements and water to the tomatoes;

Step 2: after one week of planting, culturing the tomato samples under different levels of water stress for three days, while keeping the nutrient elements unchanged;

Step 3: performing continuous tracking and detection of water stress for tomato samples under water stress, performing micro-CT detection and acquiring micro-CT feature parameters, to obtain pore size and density, thickness of cavernous body, palisade tissue, cilia density, and cross-sectional structure of vascular bundles of plant leaves and stems, volume of root system, and density and distribution parameters of main root and root hair; performing polarization-hyperspectral imaging and acquiring feature parameters from the polarization-hyperspectral images, to obtain plant crown width, plant height, and leaf inclination angle images, distribution of leaf vein, average greyscale, shadow area of leaf margin at 1,450 nm hyperspectral water-sensitive wavelength, and polarization state, Stock vector, and Muller matrix variables of the crown layer of plant samples under water stress in 1,450 nm feature images at 0°, 45°, 90°, 135°, and 180° characteristic polarization angles;

Step 4: carrying out conventional physical and chemical detections: measuring the water content in the plants with a dry-wet weight method; using SEM and micro-imaging techniques to obtain measured values of density of pore and cilia density, thickness of cavernous body and palisade tissue, and distribution density and diameter of vascular bundle, etc. of the plants; weighing dry and wet weight of the samples to determine the true value of water content in the plants;

Step 5: carrying out normalization of the feature variables of micro-CT and the feature variables of the polarization-hyperspectral images extracted in step 3, to unify the range of the feature values to 0 to 1;

Step 6: carrying out feature dimension reduction and optimization of the normalized feature parameters extracted in step 5 by means of principal component analysis in combination with piecewise and stepwise regression method; based on a principle of correlation and independence, at a significance level $\alpha=0.005$, keeping a variable if $F>4.14$ when the variable is taken into the model, weeding out a variable if $F<2.91$ in the model during the discrimination, while maintaining $R2>0.9$ (here, F is the significance coefficient of the linear relationship and R2 is the correlation coefficient in the regression model using statistical methods); carrying out feature optimization based on optimization principles of maximum correlation, minimum multi-collinearity, and minimum relative detection error, to obtain optimal feature variables as feature variables for diagnosis of water stress of the plants;

Step 7: utilizing a support vector machine regression (SVR) method to carry out feature layer fusion, and establishing an accurate and quantitative water stress detection model with multi-feature fusion based on feature variables of the pores, cavernous body, palisade tissue, cilia, vascular bundle, volume of root system, density of main root and root hair acquired with the micro-CT system, the crown width, plant height, leaf inclination angle, and distribution of leaf vein, average greyscale and shadow area of leaf margin at 1,450 nm hyperspectral water-sensitive wavelength acquired with the polarization-hyperspectral imaging system; the polarization state, Stock vector, and Muller matrix variables of plants in the 1,450 nm feature images at 0°, 45°, 90°, 135°, and 180° characteristic polarization angles;

Step 8: acquiring feature variables from the micro-CT image and polarization-hyperspectral images of the tomato samples according to step 3, and utilizing the accurate and quantitative water stress detection model with multi-feature fusion established in step 7 to carry out the detection of water stress in the greenhouse.

Furthermore, the method for micro-CT detection and acquisition of micro-CT feature parameters is as follows:

(1) Placing five tomato samples under different levels of water stress on a rotating sample bracket in a sample chamber of the Micro-CT scanning and imaging system sequentially, starting the Micro-CT scanning and imaging system via a control computer and performing scanning sequentially, to obtain CT profiles of the samples respectively;
(2) Using IPL software to select the boundaries and contours in the CT images of the samples;
(3) Selecting different tomography sections for image analysis, adjusting the high and low thresholds according to the different grayscale levels of the target in the CT image, selecting a threshold range for the target, and binarizing the CT image of the target tomato sample;
(4) Using the IPL software in combination with image analysis to obtain feature parameters of the plant leaves and stems, including pore size and density, thickness of cavernous body, palisade tissue and cilia density, and cross-sectional structure of vascular bundle, etc.;
(5) Removing the pearlite substrate on the basis of the selected boundaries and thresholds, generating a three-dimensional image of the root system, and carrying out IPL language to export parameters including volume of root system, and density and distribution of main root and root hair.

Furthermore, the method for polarization-hyperspectral detection and acquisition of feature parameters in the polarization-hyperspectral detection is as follows:
(1) Placing the sample on a double coordinate sample table of the polarization-hyperspectral imaging system, setting the wavelength range of a visible light-near infrared light source system 11 to 300 to 2,200 nm and setting the light intensity range to 0 to 6,500 lux;
(2) Using two hyperspectral imaging systems with pre-polarization filters, and setting the sampling polarization angles of the polarization filters to 0°, 45°, 90°, 135°, and 180° respectively; using hyperspectral pre-filters with 1,450 nm transmission wavelength, and performing push-broom scanning and imaging in horizontal plane direction and vertical plane direction respectively, to obtain front-view and top-view polarization-hyperspectral feature images of the plant;
(3) Extracting hyperspectral feature images of the sample under water stress in front view and top view fields, and extracting crown width, plant height and leaf inclination angle images of the plant by means of coordinate matching and front-view/top-view feature image fusion;
(4) Extracting a hyperspectral feature image of the crown layer at the characteristic wavelength, extracting feature parameters such as distribution of leaf vein, average greyscale, and shadow area of leaf margin, etc. of the leaf surface at 1,450 nm hyperspectral water-sensitive wavelength, based on the 1,450 nm pre-filters;
(5) Extracting the polarization state, Stock vector, and Muller matrix variables of the crown layer of the sample under water stress, based on the acquired 1,450 nm polarization-hyperspectral image at 0°, 45°, 90°, 135°, and 180° characteristic polarization angles.

In the water stress detection method for tomatoes in seedling stage based on micro-CT and polarization-hyperspectral multi-feature fusion, and in the micro-CT scanning and imaging system, the rotating sample bracket is fixed to the bottom of the detection sample chamber by screws at the four corners of a base, a rotating shaft is mounted at the geometrical center of the base of the rotating sample bracket, and a round sample bracket is mounted and fixed at the tail end of the rotating shaft; during the detection, the rotating shaft drives the rotating sample bracket to rotate within 100° angle range, at the same time, an X-ray emitter fixed to the middle part of the emission chamber accomplishes a CT slice scanning process of the sample by pitching motion.

In the water stress detection method for tomatoes in seedling stage based on micro-CT and polarization-hyperspectral multi-feature fusion, the polarization-hyperspectral imaging system includes a control system, a double coordinate sample table, an image acquisition system, and a light source system, Wherein the image acquisition system includes two polarization-hyperspectral imaging systems, an image acquisitor, a vertical arm, and a cantilever; the vertical arm consists of a first base, a vertical pole with a lead screw, and a first slide block, wherein the first base is fixed to the left side of the bottom of a light box by screws, the top part of the first base is connected to the vertical pole via a hinge, and the vertical pole can swing left and right using the hinge as a center, so as to accomplish spatial position adjustment of the imaging device; the first slide block is mounted on the vertical pole; a first polarization-hyperspectral imaging system is mounted on the first slide block, the first slide block can be driven by the lead screw to move up and down along the vertical pole, so that it drives the first polarization-hyperspectral imaging system to seek for an optimal detection position, to realize the acquisition of polarization-hyperspectral image information in a front view direction;

The cantilever consists of a second base, a cross rod with a lead screw and a second slide block, wherein the second base is fixed to the top part of a right side plate of the light box by screws, the second base is connected to the cross rod via a hinge, and the cross rod can swing up and down using the hinge as a center, so as to accomplish spatial position adjustment of the imaging device; the second slide block is mounted on the cross rod, a second polarization-hyperspectral imaging system is mounted on the second slide block, the second slide block can be driven by the lead screw to move left and right in the horizontal direction along the cross rod, so that it drives the second polarization-hyperspectral imaging system to seek for an optimal detection position, to realize the acquisition of polarization-hyperspectral image information in a top view direction;

Wherein the light source system consists of visible light-near infrared light sources and cloud platforms, each cloud platform is mounted on the bottom end and top end of the vertical pole and the right end and left end of the vertical pole respectively, a visible light-near infrared light source is mounted on each cloud platform respectively, and the pitching angle of the visible light-near infrared light source can be set via the cloud platform, so as to perform imaging of the plant clearly in uniform light;

The double coordinate sample table is fixed to the geometrical center of the bottom plane of the light box, and has a horizontal lead screw and a vertical lead screw, and a sample bracket is mounted on the top end of the vertical lead screw to place a sample to be detected; the sample bracket may be driven by the movement of the horizontal lead screw and the vertical lead screw to displace in the horizontal direction and the vertical direction at a constant speed, so that it works with an image acquisition control system to realize a push-broom polarization-hyperspectral imaging system and the scanning and imaging of the polarization-hyperspectral imaging system;

Wherein the polarization-hyperspectral imaging system includes a pre-polarization filter, a polarization filter driving device, pre-filters, a filter switching device, a spectrograph, and an imaging system from the front side to the rear side respectively, the polarization filter is at the most front end of the entire system, and is driven by the polarization driving device to rotate within a 100° angle range, so that the polarization angle can be set freely, and the spectrograph and the imaging system can realize the setting of polarization angle and the acquisition of stepwise polarization information; 560 nm and 1,450 nm narrow-band filters are arranged behind the polarization filter, and the filters may be switched by means of a turning wheel, and can work with the spectrograph and the imaging system to realize acquisition of hyperspectral nutrition and water stress feature images of the crop sample in front view and top view;

The control system includes a control computer, a light source controller, an image acquisitor, and a movement controller;

Wherein the light source controller is connected to the visible light-near infrared light sources to realize light source control at different light intensities with different light qualities;

The image acquisitor is connected to the two polarization-hyperspectral imaging systems and the control computer, and the control computer issues commands to carry out the acquisition and analysis of the imaging information of the polarization-hyperspectral imaging systems in front view and top view;

The double coordinate sample table, the vertical arm, the cantilever and the cloud platform is connected by the movement controller; in addition, the movement controller is connected to the control computer, the control computer issues commands to control the vertical and horizontal displacements of the double coordinate sample table, control the driving of the slide blocks of the vertical arm and the cantilever, and control the pitching angles of the PTZ.

Benefits of the Present Invention

1. The present invention utilizes micro-CT to scan the micro-morphological features of feature variables of tomatoes under water stress, such as pores, cavernous body, palisade tissue, cilia, vascular bundle, volume of root system, density of main root and root hair, etc., and simultaneously utilizes double polarization-hyperspectral imaging systems to obtain the macro-morphological features of tomatoes under water stress, such as crown width, plant height and leaf inclination angle, etc., and distribution of leaf vein, average greyscale, and shadow area of leaf margin at 1,450 nm hyperspectral water-sensitive wavelength, and polarization state, Stock vector, and Muller matrix variables, etc. in 1,450 nm feature images at 0°, 45°, 90°, 135°, and 180° characteristic polarization angles, to obtain multi-feature macro-morphological features of growth; fuses the internal and external structures, above-ground and underground, macro and micro morphological features of the crop under water stress and the characteristic wavelength image and polarization state of the crop under water stress to utilize their complementary advantages, to realize comprehensive and accurate extraction and accurate and quantitative analysis of water stress characteristics of tomatoes, and to provide a scientific basis for scientific management and control of water, fertilizer and environment in greenhouses.

2. At the same time, the present invention innovatively uses micro-CT to obtain micro-scale information of tomatoes under water stress, extracts micro-morphological features of feature variables such as pores, cavernous body, palisade tissue, cilia, vascular bundle, volume of root system, density of main root and root hair as well as features of above-ground and underground portions of the plant under water stress, and thereby realizes water stress diagnosis based on micro-scale features of tomatoes for the first time. Compared with the traditional water stress feature extraction and diagnosis method, the method provided in the present invention greatly improves the accuracy of detection of micro-morphological features under water stress.

3. Besides, the present invention innovatively utilizes polarization-hyperspectral imaging detection technology to obtain polarization-hyperspectral image information of tomato plants under water stress in different viewing fields at different polarization angles, so as to obtain macro-morphology of crown layer area, plant height, and leaf inclination angle, etc., and polarization-hyperspectral reflection image features of the plants at 1,450 nm sensitive wavelength at a characteristic incident detection angle, reflects the influences of water stress on the internal tissues and structures and their reflection and polarization characteristics. The method realizes accurate extraction of macro-morphology of the plants under water stress and multi-dimensional image features at a sensitive wavelength, and greatly improves the accuracy of detection based on macro-features.

In the figures: 1—rotating sample bracket; 2—sample; 3—X-ray emitter; 4—computer; 6—double coordinate sample table; 7—vertical arm; 7-1—first base; 7-2—vertical pole; 7-3—first slide block; 8—cantilever; 8-1—second base; 8-2—hanger rod; 8-3—second slide block; 9—polarization-hyperspectral imaging system; 9-1—first polarization-hyperspectral imager; 9-2—second polarization-hyperspectral imager; 10 cloud platform; 11—visible light-near infrared light source; 12—movement controller; 13—image acquisitor; 14—light source controller; 15—control computer

EMBODIMENTS

Hereunder the present invention will be further detailed in embodiments with reference to the accompanying drawings, but the protection scope of the present invention is not limited to those embodiments.

Figure 1:
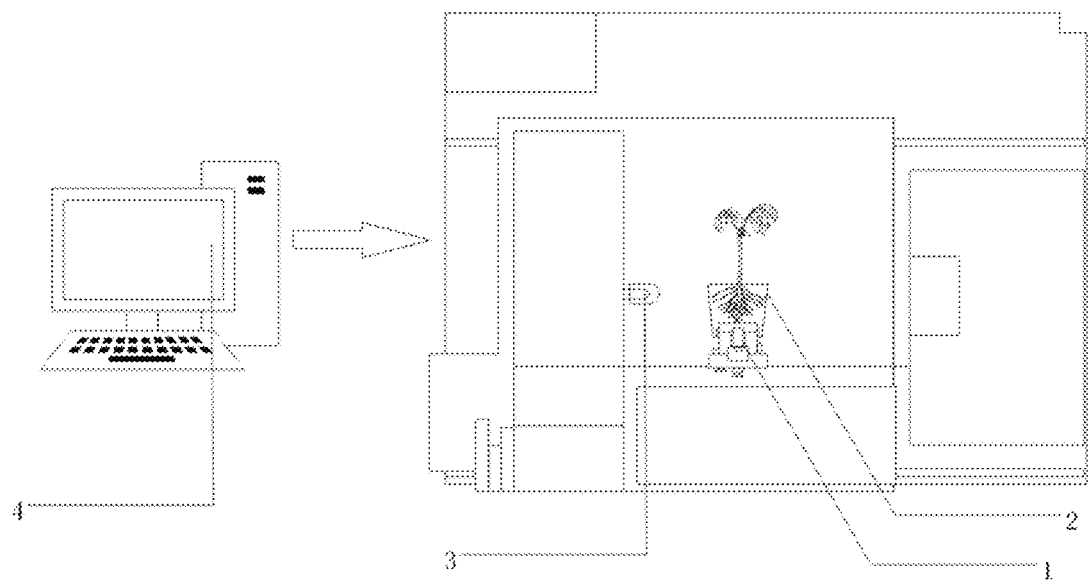
FIG. 1 is a schematic structural diagram of the micro-CT scanning and imaging system employed in the present invention.
Figure 2:
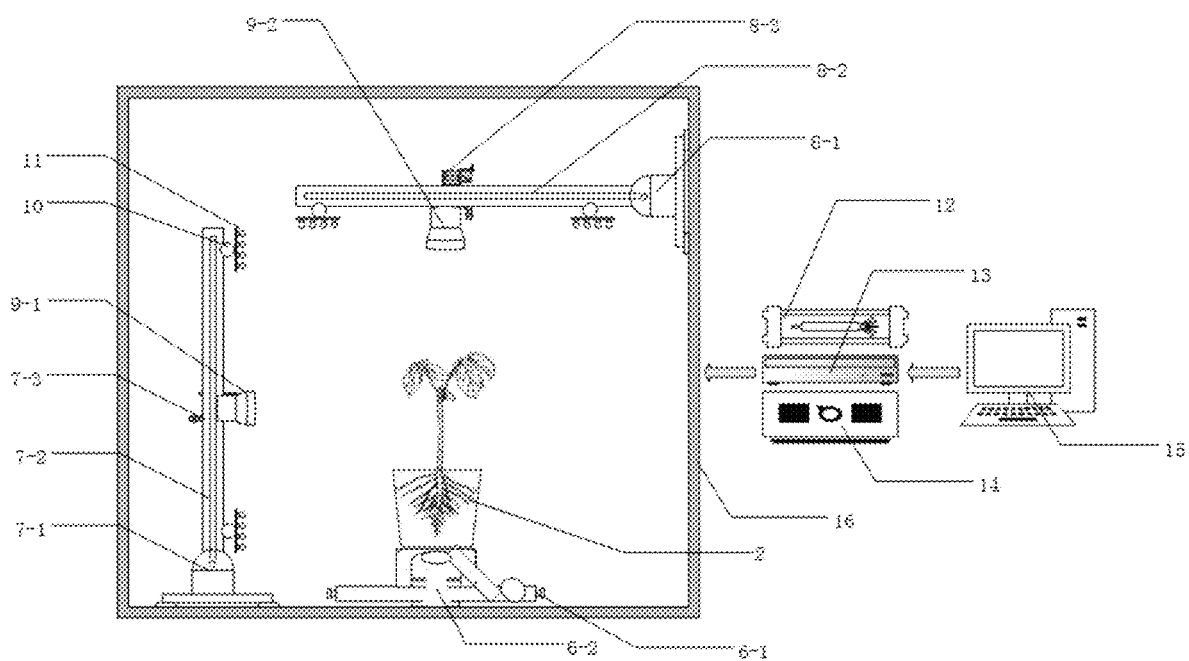
FIG. 2 is a schematic structural diagram of the polarization-hyperspectral imaging system in the present invention.

The water stress detection method for tomatoes in seedling stage based on micro-CT and polarization-hyperspectral imaging multi-feature fusion described in the present invention utilizes the micro-CT scanning and imaging system shown in FIG. 1 and the polarization-hyperspectral imaging system shown in FIG. 2 for information acquisition.

The micro-CT scanning and imaging system is shown in FIG. 1, the rotating sample bracket 1 is fixed to the bottom of the detection sample chamber by screws at the four corners of a base, a rotating shaft is mounted at the geometrical center of the base of the rotating sample bracket 1, and a round sample bracket is mounted and fixed at the tail end of the rotating shaft; during the detection, the rotating shaft drives the rotating sample bracket 1 to rotate within 360° angle range, at the same time, an X-ray emitter 3 fixed to the middle part of the emission chamber accomplishes a CT slice scanning process of the sample by pitching motion.

FIG. 2 is a polarization-hyperspectral imaging system designed for sample collection applied by the invention includes a control system, a double coordinate sample table 6, an image acquisition system, and a light source system.

Wherein the image acquisition system includes two polarization-hyperspectral imaging systems 9, an image acquisitor 12, a vertical arm 7, and a cantilever 8; the vertical arm 7 consists of a first base 7-1, a vertical pole 7-2 with a lead screw, and a first slide block 7-3, wherein the first base 7-1 is fixed to the left side of the bottom of a light box 16 by screws, the top part of the first base 7-1 is connected to the vertical pole 7-2 via a hinge, and the vertical pole 7-2 can swing left and right using the hinge as a center, so as to accomplish spatial position adjustment of the imaging device; the first slide block 7-3 is mounted on the vertical pole 7-2; a first polarization-hyperspectral imaging system 9-1 is mounted on the first slide block 7-3, the first slide block 7-3 can be driven by the lead screw to move up and down along the vertical pole 7-2, so that it drives the first polarization-hyperspectral imaging system 9-1 to seek for an optimal detection position, to realize the acquisition of polarization-hyperspectral image information in a front view direction;

The cantilever 8 consists of a second base 8-1, a cross rod 8-2 with a lead screw and a second slide block 8-3, wherein the second base 8-1 is fixed to the top part of a right side plate of the light box 16 by screws, the second base 8-1 is connected to the cross rod 8-2 via a hinge, and the cross rod 8-2 can swing up and down using the hinge as a center, so as to accomplish spatial position adjustment of the imaging device; the second slide block 8-3 is mounted on the cross rod 8-2, a second polarization-hyperspectral imaging system 9-2 is mounted on the second slide block 8-3, the second slide block 8-3 can be driven by the lead screw to move left and right in the horizontal direction along the cross rod 8-2, so that it drives the second polarization-hyperspectral imaging system 9-2 to seek for an optimal detection position, to realize the acquisition of polarization-hyperspectral image information in a top view direction;

Wherein the light source system consists of visible light-near infrared light sources 11 and cloud platforms 10, each cloud platform 10 is mounted on the bottom end and top end of the vertical pole 7-2 and the right end and left end of the vertical pole 8-2 respectively, a visible light-near infrared light source 11 is mounted on each cloud platform 10 respectively, and the pitching angle of the visible light-near infrared light source 11 can be set via the cloud platform 10, so as to perform imaging of the plant clearly in uniform light;

The double coordinate sample table 6 is fixed to the geometrical center of the bottom plane of the light box 16, and has a horizontal lead screw 6-1 and a vertical lead screw 6-2, and a sample bracket is mounted on the top end of the vertical lead screw 6-2 to place a sample 5 to be detected; the sample bracket may be driven by the movement of the horizontal lead screw 6-1 and the vertical lead screw 6-2 to displace in the horizontal direction and the vertical direction at a constant speed, so that it works with an image acquisition control system to realize a push-broom polarization-hyperspectral imaging system 9-1 and the scanning and imaging of the polarization-hyperspectral imaging system 9-2;

Wherein the polarization-hyperspectral imaging system 9 includes a pre-polarization filter, a polarization filter driving device, pre-filters, a filter switching device, a spectrograph, and an imaging system from the front side to the rear side respectively, the polarization filter is at the most front end of the entire system, and is driven by the polarization driving device to rotate within a 100° angle range, so that the polarization angle can be set freely, and the spectrograph and the imaging system can realize the setting of polarization angle and the acquisition of stepwise polarization information; 560 nm and 1,450 nm narrow-band filters are arranged behind the polarization filter, and the filters may be switched by means of a turning wheel, and can work with the spectrograph and the imaging system to realize acquisition of hyperspectral nutrition and water stress feature images of the crop sample in front view and top view;

The control system includes a control computer 15, a light source controller 14, an image acquisitor 13, and a movement controller 12;

Wherein the light source controller 14 is connected to the visible light-near infrared light sources 11 to realize light source control at different light intensities with different light qualities;

The image acquisitor 13 is connected to the two polarization-hyperspectral imaging systems 9 and the control computer 15, and the control computer 15 issues commands to carry out the acquisition and analysis of the imaging information of the polarization-hyperspectral imaging systems in front view and top view;

The double coordinate sample table 6, the vertical arm 7, the cantilever 8 and the cloud platform 10 is connected by the movement controller 12; in addition, the movement controller 12 is connected to the control computer 15, the control computer 15 issues commands to control the vertical and horizontal displacements of the double coordinate sample table, control the driving of the slide blocks of the vertical arm 7 and the cantilever 8, and control the pitching angles of the cloud platform 10.

Figure 3:
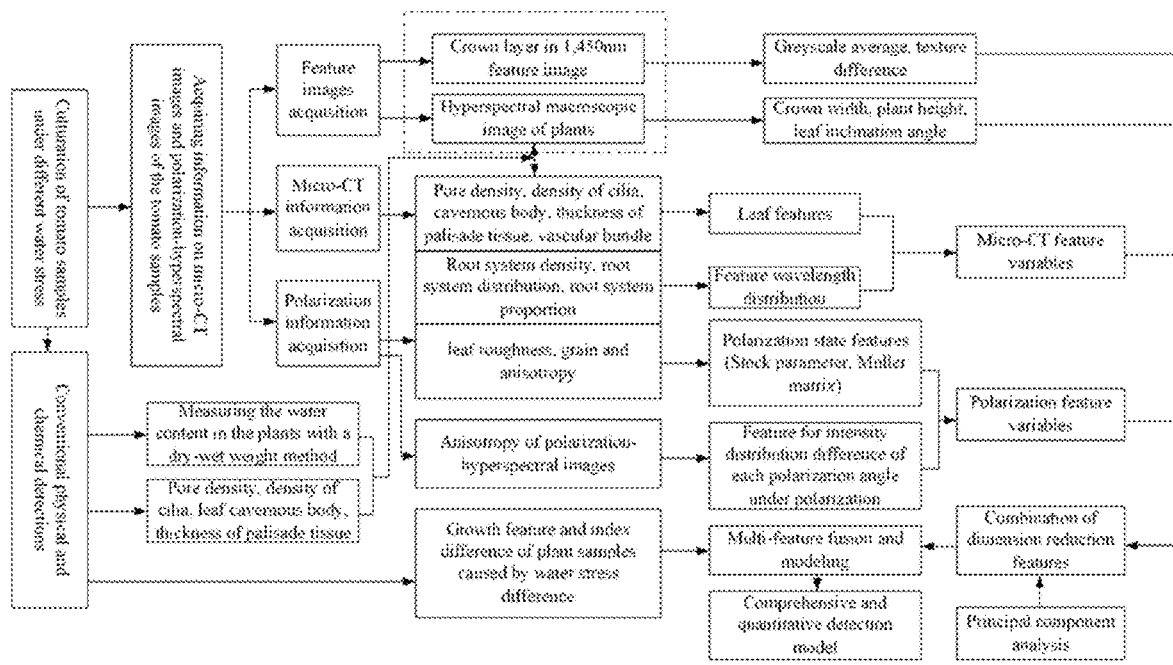
FIG. 3 is a flow chart of the water stress detection method for tomatoes in seedling stage based on micro-CT and polarization-hyperspectral imaging multi-feature fusion in the present invention.

A water stress detection method for tomatoes in seedling stage based on micro-CT and polarization-hyperspectral imaging multi-feature fusion shown in FIG. 3, including the following steps:

Step 1: using a standard nutrient solution formulation, utilizing pearlite as a substrate, employing soilless cultivation to plant tomatoes, and managing the tomatoes with standardized management methods of greenhouse to ensure normal supply of nutrient elements and water to the tomatoes;

Step 2: after one week of planting, culturing the tomato samples under different levels of water stress for three days, while keeping the nutrient elements unchanged;

Step 3: After three days of water stress on tomatoes seedling samples, micro-ct and polarization-hyperspectral images of the samples were collected in sequence, according to the following steps:

1. Micro-Ct Detection Procedures:

① Placing five tomato samples 2 under different levels of water stress on a rotating sample bracket 1 in a sample chamber of the Micro-CT scanning and imaging system sequentially, starting the Micro-CT scanning and imaging system via a control computer 4 and performing scanning sequentially, to obtain CT profiles of the samples respectively;

② Using IPL software to select the boundaries and contours in the CT images of the samples ③ Selecting different tomography sections for image analysis, adjusting the high and low thresholds according to the different grayscale levels of the target in the CT image, selecting a threshold range for the target, and binarizing the CT image of the target tomato sample;

④ Using the IPL software in combination with image analysis to obtain feature parameters of the plant leaves and stems, including pore size and density, thickness of cavernous body, palisade tissue and cilia density, and cross-sectional structure of vascular bundle, etc.;

⑤ Removing the pearlite substrate on the basis of the selected boundaries and thresholds, generating a three-dimensional image of the root system, and carrying out IPL language to export parameters including volume of root system, and density and distribution of main root and root hair.

2. Polarization-Hyperspectral Detection Procedure:

After micro-et scanning images were obtained and feature extraction was completed, samples were successively taken out for polarization-hyperspectral image scanning:

① Placing the sample on a double coordinate sample table 6 of the polarization-hyperspectral imaging system, setting the wavelength range of a visible light-near infrared light source system 11 to 300 to 2,200 nm and setting the light intensity range to 0 to 6,500 lux;

② Using two hyperspectral imaging systems 9-1 and 9-2 with pre-polarization filters, and setting the sampling polarization angles of the polarization filters to 0°, 45°, 90°, 135°, and 180° respectively; using hyperspectral pre-filters with 1,450 nm transmission wavelength, and performing pushbroom scanning and imaging in horizontal plane direction and vertical plane direction respectively, to obtain front-view and top-view polarization-hyperspectral feature images of the plant;

③ Extracting hyperspectral feature images of the sample under water stress in front view and top view fields, and extracting crown width, plant height and leaf inclination angle images of the plant by means of coordinate matching and front-view/top-view feature image fusion;

④ Extracting a hyperspectral feature image of the crown layer at the characteristic wavelength, extracting feature parameters such as distribution of leaf vein, average greyscale, and shadow area of leaf margin, etc. of the leaf surface at 1,450 nm hyperspectral water-sensitive wavelength, based on the 1,450 nm pre-filters;

⑤ Extracting the polarization state, Stock vector, and Muller matrix variables of the crown layer of the sample under water stress, based on the acquired 1,450 nm polarization-hyperspectral image at 0°, 45°, 90°, 135°, and 180° characteristic polarization angles.

Step 4: carrying out conventional physical and chemical detections: measuring the water content in the plants with a dry-wet weight method; using SEM and micro-imaging techniques to obtain measured values of density of pore and cilia density, thickness of cavernous body and palisade tissue, and distribution density and diameter of vascular bundle, etc. of the plants; weighing dry and wet weight of the samples to determine the true value of water content in the plants;

Step 5: carrying out normalization of the feature variables of micro-CT and the feature variables of the polarization-hyperspectral images extracted in step 3, to unify the range of the feature values to 0 to 1;

Step 6: carrying out feature dimension reduction and optimization of the normalized feature parameters extracted in step 5 by means of principal component analysis in combination with piecewise and stepwise regression method; based on a principle of correlation and independence, at a significance level $\alpha=0.005$, keeping a variable if $F>4.14$ when the variable is taken into the model, weeding out a variable if $F<2.91$ in the model during the discrimination, while maintaining $R^2>0.9$; carrying out feature optimization based on optimization principles of maximum correlation, minimum multi-collinearity, and minimum relative detection error, to obtain optimal feature variables as feature variables for diagnosis of water stress of the plants;

Step 7: utilizing a support vector machine regression (SVR) method to carry out feature layer fusion, and establishing an accurate and quantitative water stress detection model with multi-feature fusion based on feature variables of the pores, cavernous body, palisade tissue, cilia, vascular bundle, volume of root system, density of main root and root hair acquired with the micro-CT system, the crown width, plant height, leaf inclination angle, and distribution of leaf vein, average greyscale and shadow area of leaf margin at 1,450 nm hyperspectral water-sensitive wavelength acquired with the polarization-hyperspectral imaging system; the polarization state, Stock vector, and Muller matrix variables of plants in the 1,450 nm feature images at 0°, 45°, 90°, 135°, and 180° characteristic polarization angles;

Step 8: acquiring feature variables from the micro-CT image and polarization-hyperspectral images of the tomato samples according to step 3, and utilizing the accurate and quantitative water stress detection model with multi-feature fusion established in step 7 to carry out the detection of water stress in the greenhouse.

While some preferred embodiments of the present invention are described above, the present invention is not limited to those embodiments. Any obvious improvement, replacement, or variation that can be made by those skilled in the art without departing from the spirit of the present invention shall be deemed as falling in the protection scope of the present invention.

The invention claimed is:

1. A water stress detection method for tomatoes in a seedling stage based on micro computed tomography (micro-CT) and polarization-hyperspectral imaging multi-feature fusion, the method comprising the following steps:

step 1: utilizing pearlite as a substrate, employing soilless cultivation to plant tomatoes by using a nutrient solution, and managing the tomatoes to ensure a supply of nutrient elements and water to the tomatoes;

step 2: after one week of planting, culturing samples of the planted tomatoes under different levels of water stress for three days, while keeping the nutrient elements unchanged;

step 3: performing continuous tracking and detection of water stress for the tomato samples under water stress, and performing imaging, the imaging comprising performing micro-CT detection to acquire micro-CT feature parameters of the tomato samples and performing polarization-hyperspectral imaging to acquire polarization-hyperspectral feature parameters of the tomato samples, the micro-CT feature parameters comprising a pore size, a pore density, a thickness of cavernous body, a palisade tissue, a cilia density, a cross-sectional structure of vascular bundles of plant leaves and stems, a volume of a root system, and density and distribution parameters of main root and root hair, and the polarization-hyperspectral feature parameters comprising a plant crown width, a plant height, leaf inclination angle images, a distribution of leaf vein, an average grayscale, a shadow area of leaf margin at 1,450 nanometers (nm) hyperspectral water-sensitive wavelength, a polarization state, a Stock vector, and Muller matrix variables of a crown layer of the tomato samples under water stress in 1,450 nm feature images at 0°, 45°, 90°, 135°, and 180° characteristic polarization angles;

step 4: measuring a water content in the tomato samples with a dry-wet weight method, using scanning electron microscope (SEM) and micro-imaging techniques to obtain measured values of density of the pore density, the cilia density, the thickness of cavernous body, the palisade tissue, and a distribution density and diameter of vascular bundle of the tomato samples, the dry-wet weight method comprising weighing dry and wet weight the tomato samples to determine a true value of the water content in the tomato samples;

step 5: carrying out a normalization of the micro-CT feature parameters and the polarization-hyperspectral feature parameters acquired in step 3 to unify a range of the micro-CT feature parameters and the polarization-hyperspectral feature parameters to 0 to 1 and obtain normalized feature parameters;

step 6: carrying out feature dimension reduction and optimization of the normalized feature parameters obtained in step 5 by means of principal component analysis in combination with a piecewise and stepwise regression method based on a principle of correlation and independence at a significance level of $\alpha=0.005$, keeping a variable if $F>4.14$ when the variable is taken into the analysis, weeding out a variable if $F<2.91$ in the analysis during discrimination, while maintaining $R2>0.9$, and carrying out feature optimization based on optimization principles of maximum correlation, minimum multi-collinearity, and minimum relative detection error to obtain optimal feature parameters, from the micro-CT feature parameters and the polarization-hyperspectral feature parameters, for diagnosis of water stress of the tomato samples, where F is a significance coefficient of a linear relationship in the piecewise and stepwise regression method and R2 is a correlation coefficient the piecewise and stepwise regression method;

step 7: utilizing a support vector machine regression (SVR) method to carry out feature layer fusion on the optimal feature parameters, and establishing an accurate and quantitative water stress detection model with multi-feature fusion based on the optimal feature parameters;

step 8: acquiring an updated set of micro-CT feature parameters of the tomato samples from the micro-CT detection and an updated set of polarization-hyperspectral feature parameters of the tomato samples from the polarization-hyperspectral imaging according to step 3, and utilizing the accurate and quantitative water stress detection model with multi-feature fusion established in step 7, along with the updated set of micro-CT feature parameters and the updated set of polarization-hyperspectral feature parameters to carry out detection of water stress in an environment having the tomatoes in the seedling stage.

2. The method according to claim 1, wherein the performing of the micro-CT detection to acquire micro-CT feature parameters of the tomato samples comprises:

(1) placing the tomato samples, comprising five tomato samples, under different levels of water stress on a rotating sample bracket in a sample chamber of a micro-CT scanning and imaging system sequentially, starting the micro-CT scanning and imaging system via a control computer and performing scanning sequentially to obtain respective CT profiles of the tomato samples;

(2) using initial program load (IPL) software to select boundaries and contours in the CT images of the tomato samples;

(3) selecting, within each CT image of the CT images of the tomato samples, different tomography sections for image analysis, adjusting a high threshold and a low threshold according to different grayscale levels of a target in the respective CT image, selecting a threshold range for the target, and binarizing the respective CT image;

(4) using the IPL software in combination with image analysis to obtain the pore size, the pore density, the thickness of cavernous body, the palisade tissue, the cilia density, and the cross-sectional structure of vascular bundle;

(5) removing, from each CT image of the CT images of the tomato samples, the substrate on a basis of the selected boundaries and high threshold and low threshold, generating a three-dimensional image of the root system, and carrying out IPL language to obtain the volume of the root system and the density and distribution parameters of the main root and root hair.

3. The method according to claim 1, wherein the performing of the polarization-hyperspectral imaging to acquire polarization-hyperspectral feature parameters of the tomato samples comprises:

(1) placing each tomato sample of the tomato samples on a double coordinate sample table of a polarization-hyperspectral imaging system, setting a wavelength range of a visible light-near infrared light source system to 300 nm to 2,200 nm and setting a light intensity range to 0 lux to 6,500 lux;

(2) using two hyperspectral imaging systems with pre-polarization filters, and setting sampling polarization angles of the polarization filters to 0°, 45°, 90°, 135°, and 180°, respectively; using hyperspectral pre-filters with 1,450 nm transmission wavelength, and performing push-broom scanning and imaging in a horizontal plane direction and a vertical plane direction to obtain front-view and top-view, respectively, polarization-hyperspectral feature images of the respective tomato sample;

(3) extracting hyperspectral feature images of the respective tomato sample under water stress in front-view and top-view fields, and extracting the plant crown width, the plant height, the leaf inclination angle images of the respective tomato sample by means of coordinate matching and front-view/top-view feature image fusion;

(4) extracting a hyperspectral feature image of the crown layer at the wavelength of 1,450 nm, and extracting the distribution of leaf vein, the average greyscale, and the shadow area of leaf margin at 1,450 nm hyperspectral water-sensitive wavelength, based on the hyperspectral pre-filters with a 1,450 nm transmission wavelength;

(5) extracting the polarization state, the Stock vector, and the Muller matrix variables of the crown layer of the respective tomato sample under water stress, based on the acquired hyperspectral image at the wavelength of 1,450 nm at 0°, 45°, 90°, 135°, and 180° characteristic polarization angles.

4. The method according to claim 2, wherein, in the micro-CT scanning and imaging system:

the rotating sample bracket is fixed to the bottom of the sample chamber by screws at four corners of a base of the rotating sample bracket;

a rotating shaft is mounted at a geometrical center of the base of the rotating sample bracket;

a round sample bracket is mounted and fixed at a tail end of the rotating shaft; and during operation, the rotating shaft drives the rotating sample bracket to rotate within a 100° angle range, and at the same time, an X-ray emitter fixed to a middle part of the sample chamber accomplishes a CT slice scanning process of the sample to be detected by pitching motion.

5. The method according to claim 3, wherein, the polarization-hyperspectral imaging system comprises a control system, a double coordinate sample table, an image acquisition system, and a light source system, wherein the image acquisition system comprises two polarization-hyperspectral imaging sub-systems, a first image acquisitor, a vertical arm, and a cantilever, wherein the vertical arm comprises a first base, a vertical pole with a first lead screw, and a first slide block, the first base being fixed to a left side of a bottom of a light box by screws, a top part of the first base being connected to the vertical pole via a first hinge, and the vertical pole being configured to swing left and right using the first hinge as a center, to accomplish spatial position adjustment of the image acquisition system, wherein the first slide block is mounted on the vertical pole, a first polarization-hyperspectral imaging sub-system is mounted on the first slide block, and the first slide block is configured to be driven by the first lead screw to move up and down along the vertical pole, so that it drives the first polarization-hyperspectral imaging sub-system to seek for an optimal detection position, to realize the acquisition of polarization-hyperspectral image information in a front view direction, wherein the cantilever comprises a second base, a cross rod with a second lead screw and a second slide block, the second base being fixed to a top part of a right side plate of the light box by screws, the second base being connected to the cross rod via a second hinge, and the cross rod being configured to swing up and down using the second hinge as a center, to accomplish spatial position adjustment of the imaging acquisition system, wherein the second slide block is mounted on the cross rod, a second polarization-hyperspectral imaging sub-system is mounted on the second slide block, and the second slide block is configured to be driven by the second lead screw to move left and right in a horizontal direction along the cross rod, to drive the second polarization-hyperspectral imaging sub-system to seek for an optimal detection position, to realize the acquisition of polarization-hyperspectral image information in a top view direction;

wherein the light source system comprises visible light-near infrared light sources and cloud platforms, each cloud platform being mounted on a bottom end and top end of the vertical pole and a right end and left end of the vertical pole, respectively, the visible light-near infrared light source being mounted on each cloud platform, respectively, and a pitching angle of the visible light-near infrared light source configured to be set via the respective cloud platform, to perform imaging of sample to be detected, clearly in uniform light, wherein the double coordinate sample table is fixed to a geometrical center of a bottom plane of the light box, a sample bracket is mounted on a top end of the first lead screw to place the sample to be detected, the sample bracket is configured to be driven by movement of the second lead screw and the first lead screw to displace in the horizontal direction and a vertical direction at a constant speed, the sample bracket is configured to work with an image acquisition control system to realize a push-broom configuration of the polarization-hyperspectral imaging system and scanning and imaging of the polarization-hyperspectral imaging system, wherein the polarization-hyperspectral imaging system comprises a pre-polarization filter, a polarization filter driving device, pre-filters, a filter switching device, a spectrograph, and an imaging system from the front side to the rear side, respectively, the polarization filter being driven by the polarization filter driving device to rotate within a 100° angle range, so that a polarization angle can be set and the spectrograph and the imaging system can realize the setting of the polarization angle and acquisition of stepwise polarization information, 560 nm and 1,450 nm narrow-band filters being arranged behind the polarization filter, wherein the 560 nm and 1,450 nm narrow-band filters are configured to be switched by means of a turning wheel, and to work with the spectrograph and the imaging system to realize acquisition of hyperspectral nutrition and water stress feature images of the sample to be detected in front view and top view, wherein the control system comprises a control computer, a light source controller, a second image acquisitor, and a movement controller, wherein the light source controller is connected to the visible light-near infrared light sources to realize light source control at different light intensities with different light qualities, wherein the second image acquisitor is connected to the two polarization-hyperspectral imaging sub-systems and the control computer, and the control computer issues commands to carry out acquisition and analysis of imaging information of the polarization-hyperspectral imaging sub-systems in front view and top view;

wherein the double coordinate sample table, the vertical arm, the cantilever, and the cloud platforms are connected by the movement controller, and wherein the movement controller is connected to the control computer, the control computer issues commands to control vertical and horizontal displacements of the double coordinate sample table, control driving of the first slide block and the second slide block, and control pitching angles of the cloud platforms.

* * * * *